(12) United States Patent
Aieta et al.

(10) Patent No.: US 10,527,552 B2
(45) Date of Patent: Jan. 7, 2020

(54) SIMULTANEOUS DETECTION OF MULTIPLE SPECTRA OF SCATTERED RADIATION

(71) Applicant: Hewlett-Packard Development Company, L.P., Houston, TX (US)

(72) Inventors: Francesco Aieta, Palo Alto, CA (US); Anita Rogacs, San Diego, CA (US); Viktor Shkolnikov, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/781,991

(22) PCT Filed: Apr. 18, 2016

(86) PCT No.: PCT/US2016/028096
§ 371 (c)(1),
(2) Date: Jun. 6, 2018

(87) PCT Pub. No.: WO2017/184109
PCT Pub. Date: Oct. 26, 2017

(65) Prior Publication Data
US 2018/0364173 A1    Dec. 20, 2018

(51) Int. Cl.
*G01N 21/65* (2006.01)
*G01J 3/02* (2006.01)
(Continued)

(52) U.S. Cl.
CPC .......... *G01N 21/658* (2013.01); *G01J 3/0205* (2013.01); *G01J 3/10* (2013.01); *G01J 3/1838* (2013.01); *G01J 3/44* (2013.01)

(58) Field of Classification Search
CPC ........ G01N 21/658; G01J 3/0205; G01J 3/10; G01J 3/1838; G01J 3/44
See application file for complete search history.

(56) References Cited

U.S. PATENT DOCUMENTS

| | | | | |
|---|---|---|---|---|
| 5,442,439 A | * | 8/1995 | Battey | G01J 3/02 |
| | | | | 356/328 |
| 5,517,302 A | * | 5/1996 | Stearns | G01J 3/42 |
| | | | | 356/326 |

(Continued)

FOREIGN PATENT DOCUMENTS

| | | | |
|---|---|---|---|
| JP | 2014010216 A | * 1/2014 | |
| WO | WO-9532408 A1 | * 11/1995 | ................ G01J 3/18 |

(Continued)

OTHER PUBLICATIONS

Gopinath, A et al., "Deterministic Aperiodic Arrays of Metal Namparticals for Surface Enhanced Raman Scatterin", Mar. 2, 2009, Optical Society of America, 13 pages.

(Continued)

*Primary Examiner* — Dominic J Bologna
(74) *Attorney, Agent, or Firm* — Wall & Tong LLP

(57) ABSTRACT

In an example, an apparatus is described that includes a light source, a holographic optical element, a sampling apparatus, and a detector. The light source is configured to emit a beam of excitation light. The holographic optical element is arranged to convert the beam of excitation light into a plurality of beams of excitation light. The sampling apparatus is arranged to project the plurality of beams of excitation light onto a surface outside the apparatus as a two-dimensional pattern of projection points. The sampling apparatus is further arranged to collect scattered radiation emitted by the surface in response to the two-dimensional pattern of projection points. The detector detects a frequency shift in the scattered radiation.

19 Claims, 5 Drawing Sheets

200

(51) Int. Cl.
    *G01J 3/10*    (2006.01)
    *G01J 3/44*    (2006.01)
    *G01J 3/18*    (2006.01)

(56) References Cited

U.S. PATENT DOCUMENTS

| | | | |
|---|---|---|---|
| 5,569,904 | A | 10/1996 | Meyers |
| 7,267,948 | B2 | 9/2007 | Vo-Dinh |
| 7,830,507 | B2 | 11/2010 | Brady et al. |
| 2002/0068018 | A1 | 6/2002 | Pepper et al. |
| 2003/0058440 | A1* | 3/2003 | Scott .................. G01J 3/10 |
| | | | 356/318 |
| 2007/0103682 | A1* | 5/2007 | Yoo ..................... G01J 3/02 |
| | | | 356/318 |
| 2011/0285991 | A1 | 11/2011 | Dal Negro |
| 2013/0094020 | A1 | 4/2013 | Li et al. |
| 2013/0120748 | A1 | 5/2013 | Li et al. |
| 2013/0330710 | A1 | 12/2013 | Omenetto et al. |
| 2014/0198314 | A1 | 7/2014 | Li et al. |
| 2015/0177151 | A1 | 6/2015 | Hu et al. |

FOREIGN PATENT DOCUMENTS

| | | | | |
|---|---|---|---|---|
| WO | WO-2010019515 A2 * | 2/2010 | ........... | A61B 5/0071 |
| WO | WO-2011091793 | 8/2011 | | |
| WO | WO-2013058739 A1 * | 4/2013 | ........... | G01N 21/658 |

OTHER PUBLICATIONS

Sercel, Jeffrey P. "Increased production using excimer lasers through enhanced beam utilization factors." Proceedings of SPIE 3274 (Jun. 1998): 183—pp. 183-192.

* cited by examiner

SIMULTANEOUS DETECTION OF MULTIPLE SPECTRA OF SCATTERED RADIATION

BACKGROUND

Raman spectroscopy is a spectroscopic technique that can be used to identify molecules in a sample. The technique relies on Raman (inelastic) scattering of emitted monochromatic light. The emitted light interacts with molecular vibrations, phonons, or other excitations in the sample, which causes the energy of the emitted photons to be shifted up or shifted down. Information about the vibrational modes in the sample can be inferred from the shift in energy. This information can, in turn, be used to identify the molecules in the sample, since vibrational information is specific to the chemical bonds and symmetry of molecules.

Although spontaneous Raman spectroscopy is a powerful molecular detection technique, Raman-scattered signals tend to be very weak. These signals can be enhanced by many orders of magnitude by using specially patterned structures that locally enhance the electric field of the light source and the emitted light. This technique is known as surface-enhanced Raman spectroscopy (SERS). In SERS, sample molecules are adsorbed on rough metal surfaces and/or by nanostructures. For instance, a liquid sample may be deposited onto a silicon or glass surface having a nanostructured noble metal surface.

DETAILED DESCRIPTION

The present disclosure broadly describes a spectrometer and associated method for simultaneously detecting multiple Raman spectra using surface-enhanced Raman spectroscopy (SERS). The presence of different analytes with similar Raman signatures can make it difficult to identify the molecular content of a sample. Moreover, some molecules may behave differently (e.g., exhibit different levels of enhancement or produce different scattered signals) when interacting with different SERS surfaces. Thus, when dealing with a sample of unknown composition, it is helpful to collect Raman spectra from the sample under many different conditions in order to improve the likelihood of capturing a distinguishable feature of each molecular component.

Examples of the present disclosure position a holographic optical element between a light source and an array of spatially varying SERS substrate regions, in order to project a two-dimensional pattern of excitation light onto the spatially varying surface. In one particular example, each projection point of the pattern is incident upon a different one of the substrate regions. Each of the substrate regions will interact differently with different molecules of the sample, thereby producing different spectra (emitted Raman scattering) for the same sample when exposed to the excitation light. The emitted Raman scattering is collected, filtered, and dispersed before being delivered to a detector. The dispersion causes each projection point of the two-dimensional pattern of light to appear to the detector as a band of light, where different horizontal coordinates along the band correspond to different frequencies of light. As a result, a plurality of spectra can be produced simultaneously in a single measurement by the spectrometer (i.e., a single delivery of measured data to the detector). Each of these spectra may, in turn, be compared to a different database corresponding to reference measurements for a different substrate region in order to identify molecules in the sample. Thus, the likelihood of identifying the sample's composition is greatly increased without increasing the number of measurements made.

Figure 1:
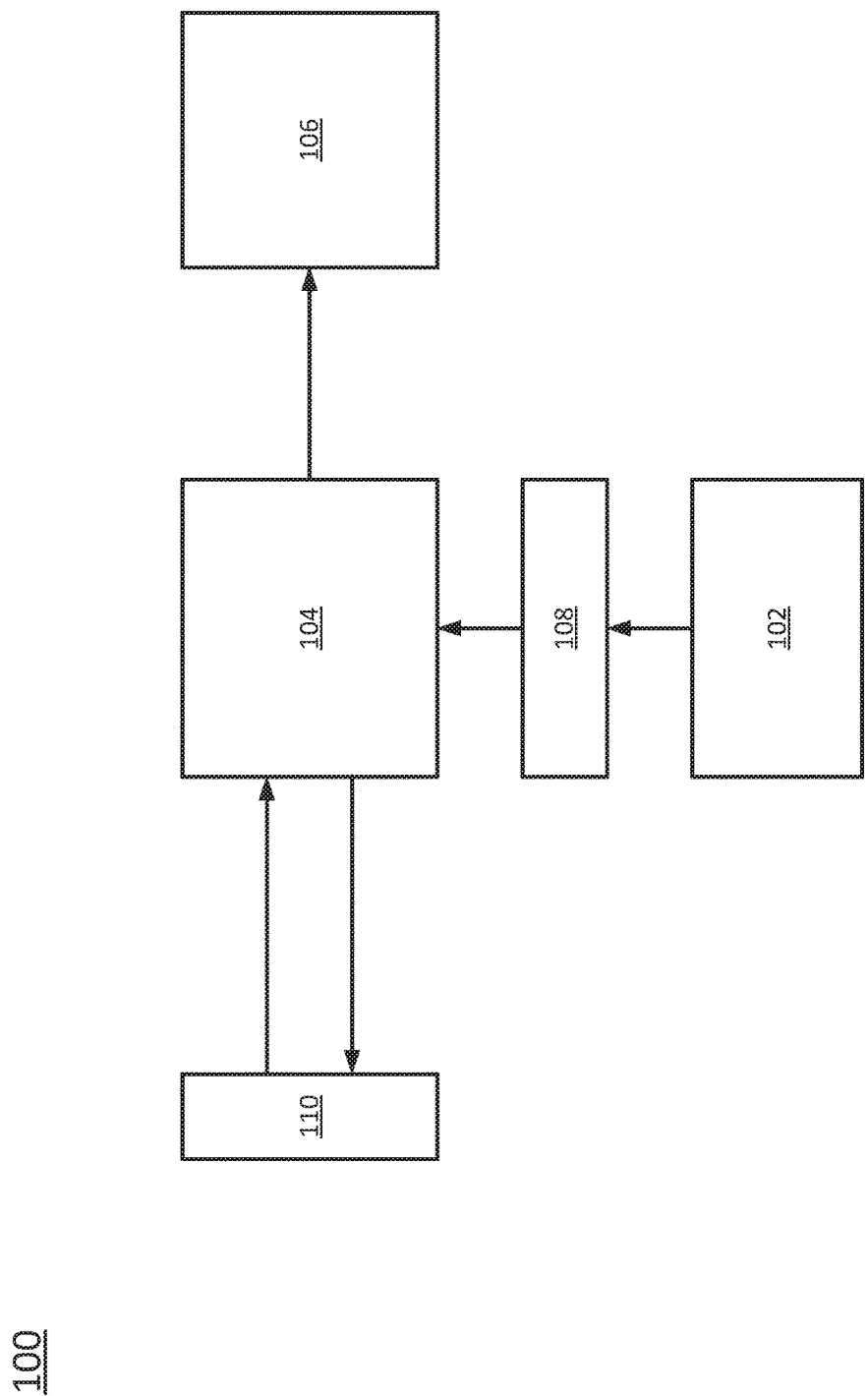
FIG. 1 is a high-level block diagram of an example spectrometer of the present disclosure.

FIG. 1 is a high-level block diagram of an example spectrometer 100 of the present disclosure. In one example, the spectrometer 100 is a Raman spectrometer. In one example, the spectrometer 100 generally includes a light source 102, a sampling apparatus 104, and a detector 106. In addition, a holographic optical element 108 is positioned between the light source 102 and the sampling apparatus 104.

In one example, the light source 102 is a laser diode that emits a beam of excitation light in the visible, near infrared, or near ultraviolet range.

The holographic optical element 108 is positioned to intercept the beam of excitation light and to convert the beam of excitation light into a plurality of beams of excitation light traveling at different angles. In one example, the holographic optical element comprises a diffractive mask that contains a superposition of diffraction gratings with different spatial frequencies.

Figure 3:
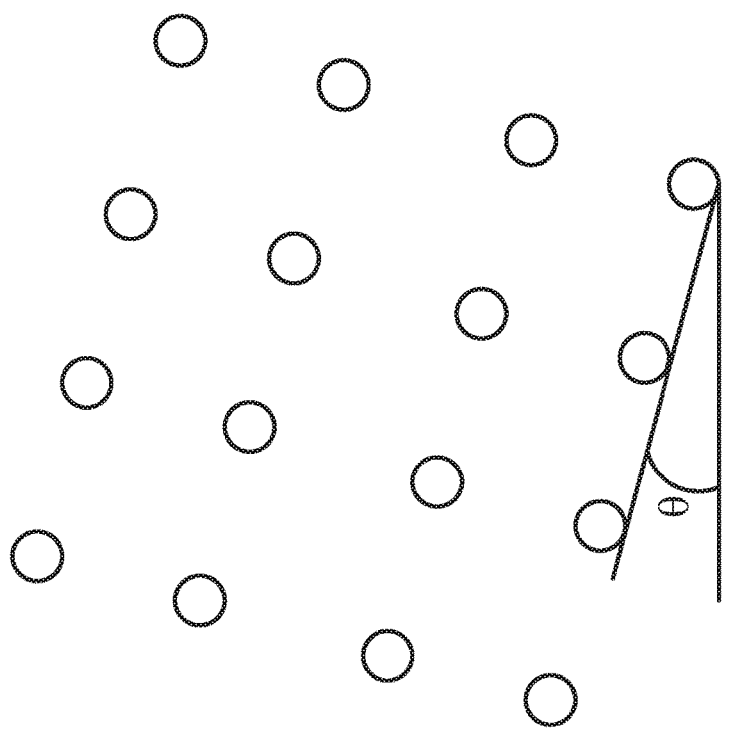
FIG. 3 illustrates an example two-dimensional pattern of excitation light that may be produced by the spectrometers of FIGS. 1 and 2 using the respective holographic optical elements.

The sampling apparatus 104 is configured to project the plurality of beams of excitation light onto a sample 110 as a two-dimensional pattern of excitation light. An example two-dimensional pattern of excitation light that may be projected is illustrated in FIG. 3. The sampling apparatus 104 is further configured to collect scattered radiation emitted by the sample 110 in response to the incidence of the two-dimensional pattern of excitation light. In one example, the sampling apparatus 104 may comprise a microscope or a fiber optic probe.

The detector 106 is configured to detect a frequency shift in the scattered radiation collected by the sampling apparatus 104. As discussed above, vibrational modes (and, consequently, molecule identities) can be detected from upward or downward shifts in frequencies. In one example, the detector comprises a charge-coupled device (CCD) detector.

Figure 2:
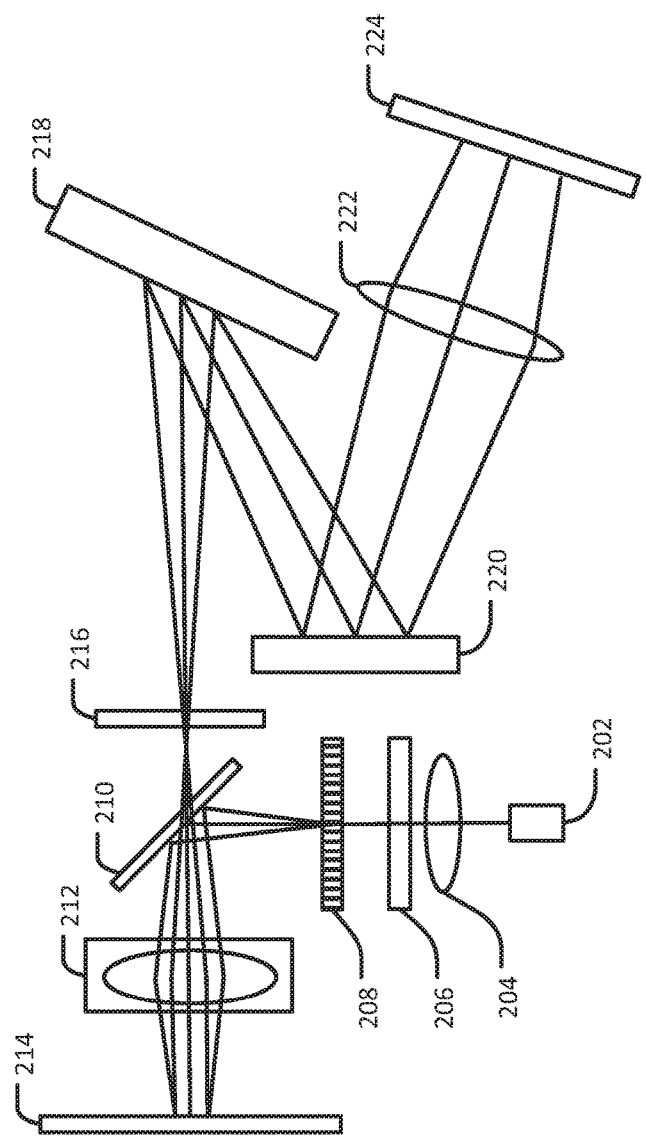
FIG. 2 is a more detailed block diagram of an example spectrometer of the present disclosure.

FIG. 2 is a more detailed block diagram of an example spectrometer 200 of the present disclosure. The spectrometer 200 may comprise a specific implementation of the spectrometer 100 illustrated in FIG. 1. Thus, in one example, the spectrometer 200 is a Raman spectrometer. In one example, the spectrometer 200 generally includes a light source 202, a first lens 204, a laser cleanup filter 206, a holographic optical element 208, a beam splitter 210, an objective lens 212, a sample port or sample tray 214, a laser blocking filter 216, a diffraction grating 218, a folding mirror 220, a focusing lens 222, and a detector 224.

In one example, the light source 202 is a laser diode that emits excitation light in the visible, near infrared, or near ultraviolet range. The first lens 204 is positioned directly in the light source's emission path and is further positioned to focus a beam of excitation light emitted by the light source 202 onto the laser cleanup filter 206.

In one example, the laser cleanup filter 206 is a laser line or narrow bandpass filter. The laser cleanup filter 206 is positioned to remove unwanted energy in the excitation light, such as secondary transmissions, background plasma, and other artifacts, and to deliver the "cleaned" beam of excitation light to the holographic optical element 208.

In one example, the holographic optical element 208 is a diffractive mask comprising a superposition of diffraction gratings with different spatial frequencies. The holographic optical element 208 is positioned to convert the cleaned beam of excitation light into a superposition of beams of excitation light traveling at different angles and to deliver these beams of excitation light to the beam splitter 210.

In one example, the beam splitter 210 is a dichroic mirrored prism. The beam splitter 210 is positioned to intercept the beams of excitation light traveling at different angles and to reflect the beams of excitation light onto the objective lens 212. The beam splitter 210 may be oriented at forty-five degrees, in order to account for an approximately ninety degree angle between the light source 202 and the objective lens 212.

The objective lens 212 is positioned to receive the beams of excitation light from the beam splitter 210 and to convert the different angles at which the beams of excitation light are traveling to different positions or locations on the sample port 214. This creates a two-dimensional pattern of excitation light at the sample port 214 that may be incident upon the surface of a sample (e.g., a sample adsorbed onto a SERS substrate) positioned at the sample port 214. An example two-dimensional pattern of excitation light that may be projected is illustrated in FIG. 3.

The sample port 214 may comprise a spectrometer output path positioned to provide excitation light to a sample, such as a sample adsorbed onto a SERS substrate. Additionally, the sample port 214 may include a tray or other mechanism configured to support the sample during measurement. As discussed above, the excitation light is incident upon a sample as a two-dimensional pattern of projection points.

A sample positioned at the sample port 214 will produce emitted Raman scattering (i.e., inelastic scattered radiation) in response to incidence of the two-dimensional pattern of excitation light. The objective lens 212, described above, is further positioned to collect the emitted Raman scattering and to deliver the emitted Raman scattering to the beam splitter 210. The beam splitter 210 is further positioned to deliver the emitted Raman scattering to the laser blocking filter 216.

In one example, the laser blocking filter 216 is a longpass edge or laser rejection filter. The laser blocking filter 216 is positioned to isolate the Raman signal by removing unwanted scattered energy in the emitted Raman scattering, such as elastic scattered radiation at the wavelength corresponding to the laser line (i.e., Rayleigh scattering), and to deliver the isolated Raman signal to the diffraction grating 218.

The diffraction grating 218 is positioned to receive the isolated Raman signal from the laser blocking filter 216 and to disperse the isolated Raman signal before delivering the dispersed isolated Raman signal to the folding mirror 220.

The folding mirror 220 is positioned to receive the dispersed isolated Raman signal from the diffraction grating 218 and to deliver the dispersed isolated Raman signal to the focusing lens 222.

The focusing lens 222 is positioned to receive the dispersed isolated Raman signal from the folding mirror 220 and to project the dispersed isolated Raman signal onto the detector 224.

In one example, the detector 224 is a charge-coupled device (CCD) detector. Due to the dispersion of the isolated Raman signal by the diffraction grating, each projection point of the two-dimensional pattern of excitation light that is incident upon a sample will appear to the detector 224 as a band of light. Different horizontal coordinates along the band of light will correspond to different frequencies, from which shifts in frequencies (and, thus, vibrational modes and molecule identities) can be detected.

In one example, the orientation angle of the two-dimensional pattern of excitation light relative to the diffraction grating 218 can be configured to optimize the fraction of the detector area that collects useful spectral data. For instance, in one example, this orientation angle is configured at fifteen degrees.

FIG. 3 illustrates an example two-dimensional pattern 300 of excitation light that may be produced by the spectrometers 100 and 200 of FIGS. 1 and 2 using the respective holographic optical elements 108 and 208. As illustrated, in one example, the two-dimensional pattern comprises a rectangular array of projection points (e.g., dots or spots), such as a four-by-four array.

The angle, θ, represents a relative orientation of the two-dimensional pattern 300 to the diffraction grating 218 of the spectrometer 200. This angle can be configured to optimize fraction of the detector area that collects useful spectral data, as discussed above. In one example, this angle is approximately fifteen degrees.

Figure 4:
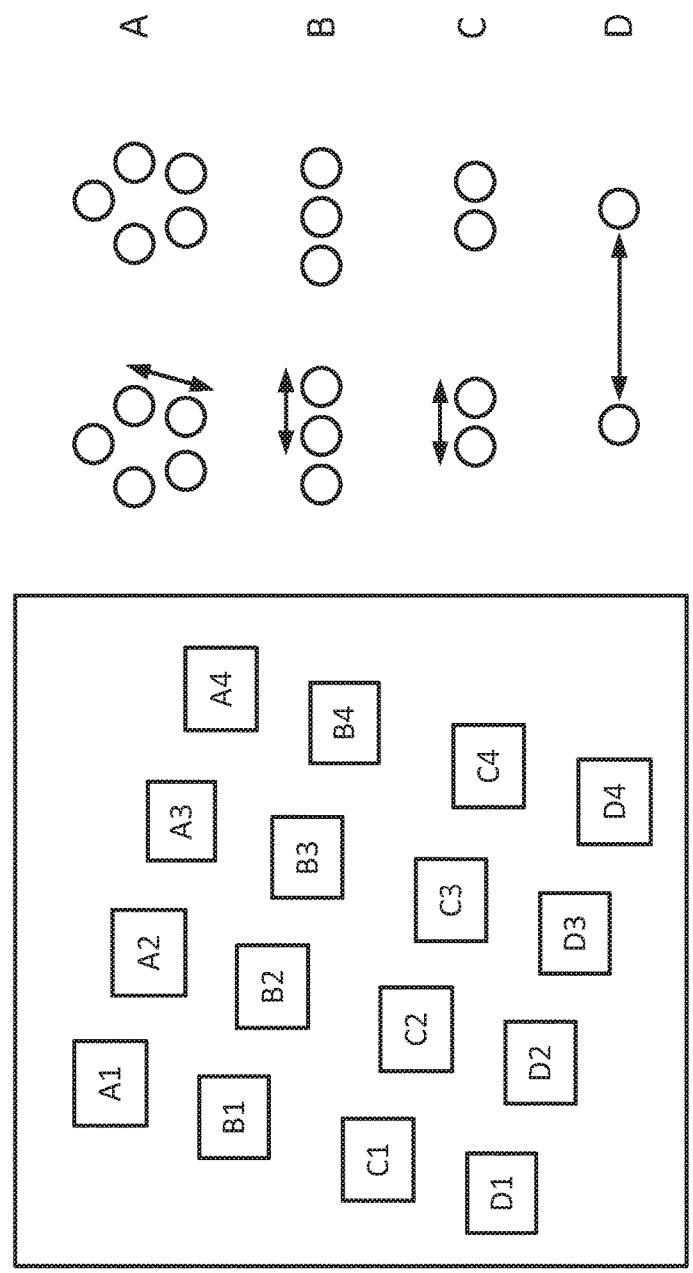
FIG. 4 illustrates an example substrate comprising an array of spatially varying regions that may be used in conjunction with the spectrometers illustrated in FIGS. 1 and 2.

FIG. 4 illustrates an example substrate 400 comprising an array of spatially varying regions A1-D4 that may be used in conjunction with the spectrometers 100 and 200 illustrated in FIGS. 1 and 2. As illustrated, the substrate 400 comprises a plurality of spatial regions A1-D4, arranged in a plurality of rows (identified by the letters A-D) and a plurality of columns (identified by the numbers 104). Although the illustrated substrate 400 comprises four rows and four columns for a total of sixteen spatial regions, any number of spatial regions, arranged in any number of rows and/or columns may be deployed.

In one example, each of the spatial regions A1-D4 comprises a SERS substrate. For example, each of the spatial regions A1-D4 may include a patterned surface structure. This patterned surface structure may be created in one example by a pattern of polymer fingers capped with metallic nanoparticles. In one example, the patterned surface is different for each of the spatial regions A1-D4. For instance, the geometry of the polymer fingers may be varied from spatial region to spatial region by changing the distance between the polymer fingers, the spatial arrangement of the polymer fingers, the size of the polymer fingers, and/or other parameters. In addition, the functional chemistries of the polymer fingers may be varied from spatial region to spatial region.

In the example illustrated in FIG. 4, for instance, each row (A-D) of the substrate 400 corresponds to a different spatial arrangement of the polymer fingers (i.e., pentamer for row A, trimer for row B, dimer for row C, and monomer for row D). In addition, each column (1-4) of the substrate 400 corresponds to a different spacing between the polymer fingers (as indicated by the arrows). By combining these parameters in different ways, sixteen unique spatial regions can be produced on the substrate 400.

In one example, the number of spatial regions on the substrate 400 is equal to the number of projection points in the two-dimensional pattern that is projected upon the substrate 400 (i.e., there is a one-to-one correspondence between the number of spatial regions and the number of projection points). The sampling apparatus 104 (or, more particularly, the objective lens 212) may project the two-dimensional pattern such that each projection point is incident upon a different one of the spatial regions.

In further examples, the functional chemistry of the patterned surface structure can be varied across the substrate 400. For instance, the fingers in one or more of the spatial regions A1-D4 may be fabricated with different surface functionalizations designed to interact with different analytes, and thus provide different spectra.

Figure 5:
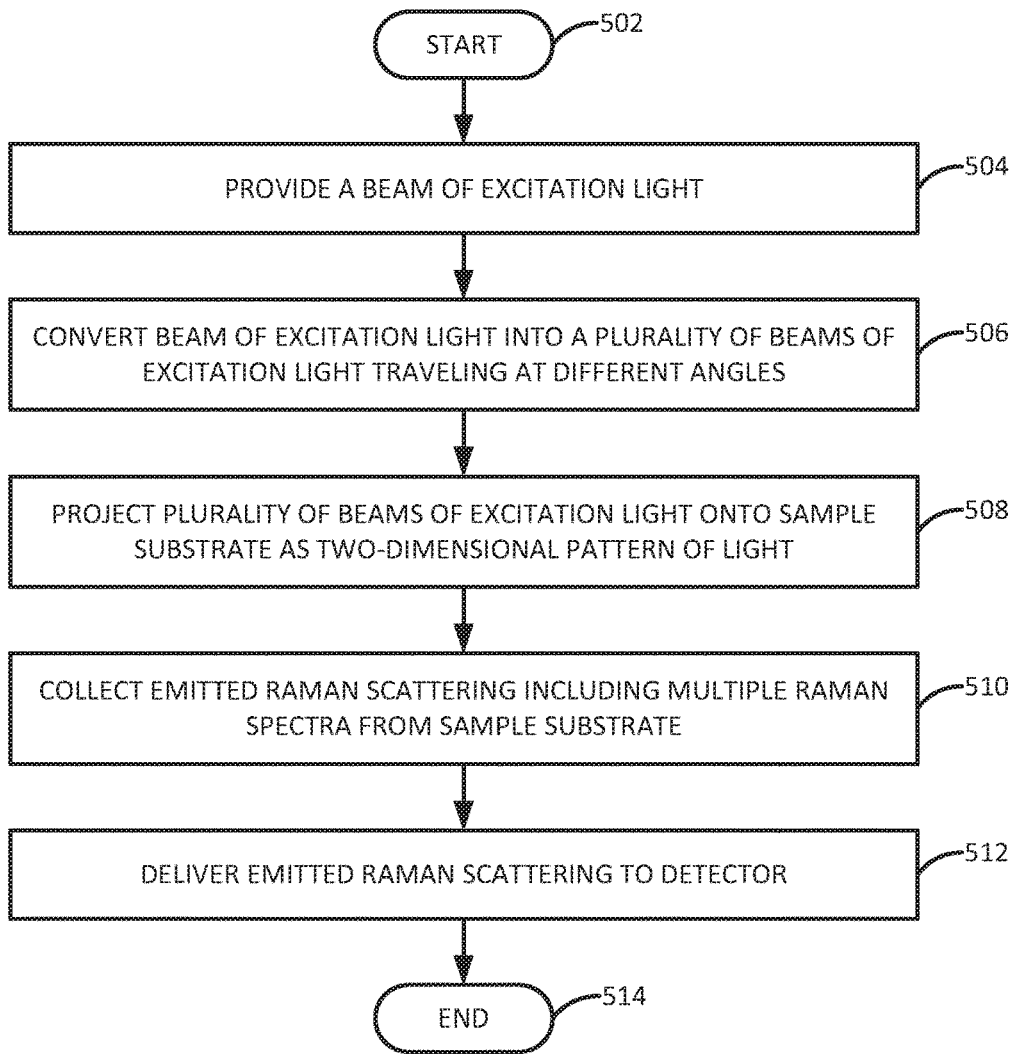
FIG. 5 illustrates a flowchart of an example method for molecular detection.

FIG. 5 illustrates a flowchart of an example method 500 for molecular detection. The method 500 may be performed, for example, by the example spectrometer 100 illustrated in FIG. 1. As such, reference in made in the discussion of the method 500 to various components of the spectrometer 100. However, the method 500 is not limited to implementation with the spectrometer illustrated in FIG. 1.

The method 500 begins in block 502. In block 504, a beam of excitation light is provided, for example by the light source 102. In one example, the beam of excitation light is a beam of visible, near infrared, or near ultraviolet radiation.

In block 506, the beam of excitation light is converted into a plurality of beams of excitation light traveling at different angles, for example by the holographic optical element 108. In one example, the single beam of excitation light may be "cleaned" to remove unwanted energy, such as secondary transmissions, background plasma, and other artifacts, prior to being converted into the plurality of beams of excitation light.

In block 508, the plurality of beams of excitation light is projected as a two-dimensional pattern of projection points onto a substrate, for example by the objective lens 212. A sample whose molecular composition is to be identified is adsorbed onto the substrate. Projection of the two-dimensional pattern may involve converting the different angles at which the plurality of beams of excitation light are traveling into different positions or locations on the substrate. For instance, in one example, the substrate comprises an array of spatially varying regions, such as the substrate 400 illustrated in FIG. 4. In this case, projection of the two-dimensional pattern includes converting each angle at which one of the plurality of beams of excitation light is traveling into a point location that is incident upon one of the spatial regions of the substrate.

In block 510, emitted Raman scattering is collected from the substrate, for example by the objective lens 212. The emitted Raman scattering is emitted by the substrate in response to the incidence of the excitation light of the two-dimensional pattern. In particular, the emitted Raman scattering is produced by interactions of the molecules of the sample that is housed upon the substrate with the excitation light. The emitted Raman scattering may be enhanced by the local surface topography of the substrate. When each region of the substrate has a different local topography, the emitted Raman scattering may vary from region-to-region. In this case, multiple Raman spectra may be collected simultaneously in block 510.

In block 512, the emitted Raman scattering is delivered to a detector, such as the detector 224. Subsequently, the detector may identify one or more molecules contained in the sample, according to the signature(s) of the emitted Raman scattering. For example, by comparing a frequency shift of the emitted Raman scattering to a database corresponding to reference measurements for a spatial region of the substrate from which the emitted Raman scattering was collected, one or more molecules of the sample may be identified. In one example, the emitted Raman scattering is isolated from unwanted scattered energy, such as elastic scattered radiation at the wavelength corresponding to the laser line (i.e., Rayleigh scattering), prior to being delivered to the detector. The emitted Raman scattering may also be dispersed, e.g., by the diffraction grating 218, prior to being delivered to the detector.

The method 500 ends in block 514.

It should be noted that although not explicitly specified, some of the blocks, functions, or operations of the method 500 described above may include storing, displaying and/or outputting for a particular application. In other words, any data, records, fields, and/or intermediate results discussed in the methods can be stored, displayed, and/or outputted to another device depending on the particular application. Furthermore, blocks, functions, or operations in FIG. 5 that recite a determining operation, or involve a decision, do not imply that both branches of the determining operation are practiced. In other words, one of the branches of the determining operation may not be performed, depending on the results of the determining operation.

Variants of the above-disclosed and other features and functions, or alternatives thereof, may be combined into many other different systems or applications. Various presently unforeseen or unanticipated alternatives, modifications, or variations therein may be subsequently made which are also intended to be encompassed by the following claims.

What is claimed is:

1. An apparatus, comprising:
    a light source for emitting a beam of excitation light;
    a holographic optical element for converting the beam of excitation light into a plurality of beams of excitation light, wherein the holographic optical element comprises a diffractive mask including a superposition of a plurality of diffractive gratings having different spatial frequencies;
    a microscope for projecting the plurality of beams of excitation light onto a surface outside the apparatus as a two-dimensional pattern of projection points and for collecting scattered radiation emitted by the surface in response to the two-dimensional pattern of projection points; and
    a detector for detecting a frequency shift in the scattered radiation.

2. The apparatus of claim 1, further comprising:
    a diffraction grating positioned between the microscope and the detector, for dispersing the scattered radiation prior to the scattered radiation being delivered to the detector.

3. The apparatus of claim 1, wherein the surface outside the apparatus comprises:
    a surface-enhanced substrate.

4. The apparatus of claim 3, wherein the surface-enhanced substrate comprises a plurality of regions, and a local topography of the substrate varies across the plurality of regions.

5. The apparatus of claim 4, wherein the local topography comprises a pattern of polymer fingers, and at least some of the polymer fingers are capped with metal nanoparticles.

6. The apparatus of claim 5, wherein variations in the local topography are created by varying a spatial arrangement of the polymer fingers across the plurality of regions.

7. The apparatus of claim 5, wherein variations in the local topography are created by varying a spacing between the polymer fingers across the plurality of regions.

8. The apparatus of claim 4, wherein the microscope is configured to arrange the two-dimensional pattern of projection points so that one of the projection points is incident upon each region of the plurality of regions.

9. The apparatus of claim 1, wherein the two-dimensional pattern of projection points comprises a rectangular array of projection points.

10. A method, comprising:
providing a beam of excitation light;
converting the beam of excitation light into a plurality of beams of excitation light using a holographic optical element comprising a diffractive mask that includes a superposition of a plurality of diffractive gratings having different spatial frequencies;
projecting the plurality of beams of excitation light onto a surface as a two-dimensional pattern of projection points;
collecting scattered radiation emitted by the surface in response to the two-dimensional pattern of projection points, wherein the scattered radiation simultaneously includes multiple spectra of scattered radiation; and
delivering the scattered radiation to a detector.

11. The method of claim 10, further comprising:
providing a surface-enhanced substrate onto which to project the two-dimensional pattern of projection points, wherein a sample containing at least one molecule is adsorbed onto the surface-enhanced substrate.

12. The method of claim 11, wherein the providing comprises:
providing a plurality of regions in the surface-enhanced substrate; and
varying a local topography of the substrate across the plurality of regions.

13. The method of claim 12, wherein the local topography comprises a pattern of polymer fingers, and at least some of the polymer fingers are capped with metal nanoparticles.

14. The method of claim 13, wherein the varying comprises:
varying a spatial arrangement of the polymer fingers across the plurality of regions; or
varying a spacing between the polymer fingers across the plurality of regions.

15. The method of claim 12, wherein the projecting comprises:
projecting one of the projection points upon each region of the plurality of regions.

16. The method of claim 10, wherein the two-dimensional pattern of projection points comprises a rectangular array of projection points.

17. An apparatus, comprising:
a light source for emitting a beam of excitation light;
a holographic optical element for converting the beam of excitation light into a plurality of beams of excitation light, wherein the holographic optical element comprises a diffractive mask including a superposition of a plurality of diffractive gratings having different spatial frequencies;
a fiber optic probe for projecting the plurality of beams of excitation light onto a surface outside the apparatus as a two-dimensional pattern of projection points and for collecting scattered radiation emitted by the surface in response to the two-dimensional pattern of projection points; and
a detector for detecting a frequency shift in the scattered radiation.

18. The apparatus of claim 17, wherein the two-dimensional pattern of projection points comprises a rectangular array of projection points.

19. The apparatus of claim 17, wherein the surface outside the apparatus comprises:
a surface-enhanced substrate.

* * * * *